(12) United States Patent
Swansen et al.

(10) Patent No.: US 6,216,363 B1
(45) Date of Patent: Apr. 17, 2001

(54) DRYING APPARATUS AND METHOD OF PREVENTING DIAPER DERMATITIS

(76) Inventors: Sara Swansen, 737 Kitterman Cir., Norwalk, IA (US) 50211; Matt Allison, 2158 Larkspur Dr., Alpine, CA (US) 91901

( * ) Notice: Subject to any disclaimer, the term of this patent is extended or adjusted under 35 U.S.C. 154(b) by 0 days.

(21) Appl. No.: 09/494,981

(22) Filed: Jan. 31, 2000

(51) Int. Cl.[7] ...................................................... F26B 5/04
(52) U.S. Cl. ................... 34/415; 34/493; 34/90
(58) Field of Search ....................... 34/283, 413, 415, 34/487, 493, 495, 90, 97; 604/368, 370, 396; 128/203.22, 203.27, 204.17

(56) References Cited

U.S. PATENT DOCUMENTS

| | | | |
|---|---|---|---|
| 4,523,589 | * 6/1985 | Krauser | 128/203.27 |
| 4,924,602 | 5/1990 | Ohlsen . | |
| 5,038,769 | * 8/1991 | Krauser | 128/203.27 |
| 5,144,757 | 9/1992 | Sasso . | |
| 5,487,877 | * 1/1996 | Choi | 422/300 |
| 5,790,749 | 8/1998 | Polaert et al. . | |
| 5,956,863 | 9/1999 | Allen . | |
| 5,984,854 | * 11/1999 | Ishikawa et al. | 600/9 |

* cited by examiner

Primary Examiner—Stephen Gravini
(74) Attorney, Agent, or Firm—Zarley, McKee, Thomte, Voorhees, & Sease

(57) ABSTRACT

A new method for treating the diapered area of a child's skin to prevent diaper dermatitis. The method features the use of a portable drying apparatus having a housing with an air admitting inlet and an air discharging outlet, a rotary impeller mechanism in the housing for creating a flow of air through the air outlet, and a handle mounted to the housing. The method employs the use of an air stream which is at or near air ambient temperature. Exposing the child's skin to air at such temperatures minimizes the risk of skin burn as a safe method for treating the diapered area. The present invention also includes an improved apparatus as referred to above.

16 Claims, 3 Drawing Sheets

DRYING APPARATUS AND METHOD OF PREVENTING DIAPER DERMATITIS

BACKGROUND OF THE INVENTION

1. Field of the Invention

The present invention relates to a method and apparatus for treating diaper dermatitis. More particularly, though not exclusively, the present invention relates to a drying apparatus and method of using the same in treating the diapered area of a child's skin to help prevent diaper dermatitis.

2. Problems in the Art

Diaper dermatitis, also known as diaper rash, is an extremely common occurrence among newborns and infants. It is the most common form of contact dermatitis in childhood and is a typical example of primary irritant contact dermatitis. Occlusion of the groin with diapers allows increased concentration of moisture in the area eventually leading to the breakdown of the underlying skin. Although diaper rash is usually mild and transient, bacteria or fungi sometimes invade the damaged skin, causing a severe diaper rash requiring medical evaluation and treatment.

The best treatment for diaper rash is prevention. Keeping the diapered area dry is an essential component of prevention. Common preventative recommendations include frequent diaper changes, use of super absorbable diapers, and allowing several minutes of air drying without the diaper. Although these prior art methods of treating the diapered area are effective for preventing diaper dermatitis, they can be impractical.

As an alternative to temporary diaper removal and air drying, a conventional hair dryer can be use to expedite the drying process. This is an effective technique; however, it presents significant safety concerns, namely the potential for skin burns even on the lowest temperature settings. Conventional hair dryers also require an AC power source and therefore can only be used in close proximity to an AC power outlet. Still further yet, conventional hair dryers tend to be bulky and are not well suited for easy transport in a diaper bag and the like.

Thus, there is a need in the art for the development of a safe and effective blow dryer or fan and method of using the same designed specifically for use on diapered areas of newborns and infants that helps prevent and halt progression of diaper rash.

3. Features of the Invention

A general feature of the present invention is the provision of an improved method and apparatus for treating the diapered area of a child's skin that helps prevent diaper dermatitis.

A further feature of the present invention is the provision of an improved method and apparatus for treating the diapered area of a child's skin that is safe in use, eliminating the risk of skin burns and other irritations on the diapered area.

A still further feature of the present invention is the provision of an improved drying apparatus for treating the diapered area of a child's skin that may be easily transported and stored in a diaper bag or similar hand bag.

A further feature of the present invention is the provision of an improved drying apparatus that is simple to use, efficient with drying, and durable.

A still further feature of the present invention is the provision of an improved drying apparatus for treating the diapered area of a child's skin that can be operated free from electrical connection with an AC power source.

These, as well as other features, objects, and advantages of the present invention will become apparent from the following specification and claims.

SUMMARY OF THE INVENTION

The present invention presents a new method for treating the diapered area of a child's skin to help prevent or reduce the severity of diaper dermatitis. The method features the use of a portable drying apparatus having a housing with an air admitting inlet and an air discharging outlet, a rotary impeller mechanism within the housing for creating a flow of air through the air outlet, and a handle mounted to the housing. A key feature of the present invention is the use of an air stream which is at or near ambient air temperature. Exposing the child's skin to air at such temperatures minimizes the risk of skin burn and is a safe method for treating the diapered area. After removing the soiled diaper and washing the diaper area of the child's skin, a caregiver can use the portable drying apparatus to dry the diapered area by directing the flow of air toward the diapered area.

The present invention also includes an improved drying apparatus as referred to above. In a preferred form, the drying apparatus is portable and does not include a heating element for heating the flow of air. Providing a drying apparatus without a heating element obviates the need to protect against the inadvertent use of heated air in drying the diapered area. A preferred form of the drying apparatus also includes a handle hingeably mounted to the housing and moveable between a projected position and retracted position. For ease of use in handling, the handle may also have a rubberized gripping surface with a plurality of ridges forming a finger mold. Still further, the drying apparatus may contain a rechargeable power source for providing power to the rotary impeller mechanism.

DETAILED DESCRIPTION OF THE PREFERRED EMBODIMENT

The present invention will be described as it applies to a preferred embodiment. It is not intended that the present invention be limited to the described preferred embodiment. It is intended that the invention cover all modifications and alternatives which may be included within the broad spirit and scope of the invention.

Figure 1:
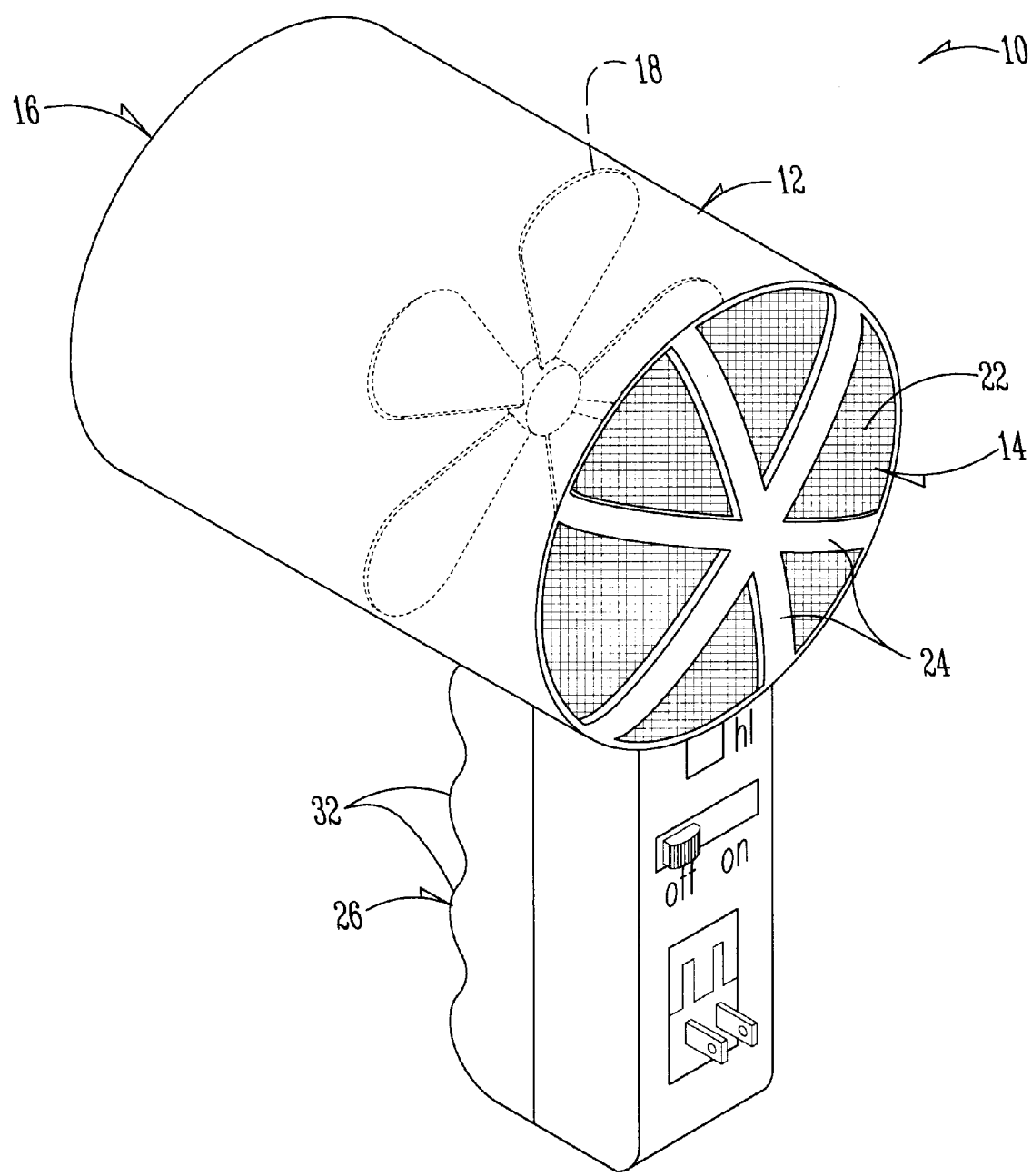
FIG. 1 is a perspective view of the drying apparatus of the present invention.

Now, referring to the drawings, FIG. 1 shows the portable drying apparatus 10 of the present invention. The drying apparatus 10 includes a hollow cylindrical housing 12 having an air inlet 14 and air outlet 16. A rotary impeller 18 is mounted within the housing 12. The impeller 18 produces a flow of air that is admitted from the air inlet 14 and discharged through the air outlet 16.

The drawings show only those parts of the portable drying apparatus 10 which are necessary for a full understanding of the invention. For example, the drawings do not show the details of the control circuit which drives the rotary impeller 18. The drawings also do not show the details of the motor. All such parts not specifically shown are of a conventional design and can be identical with those employed and presently available hair dryers.

As will be evidenced from the following description, the drying apparatus 10 of the present invention differs in several significant respects from conventional hair dryers. One important difference is that the hair drying apparatus 10 of the present invention does not include a heating element. Conventional hair dryers employ an electric heating unit that warms the air between the air inlet 14 and air outlet 16. Exposing the diapered area of a child's skin to hot air discharged from prior art hair dryers can irritate the child's skin, resulting in skin burns or other skin irritations. For this reason, the drying apparatus 10 of the present invention does not include a heating element. As such, the drying apparatus 10 produces and discharges a flow of air that is at or near ambient air temperature.

Figure 2:
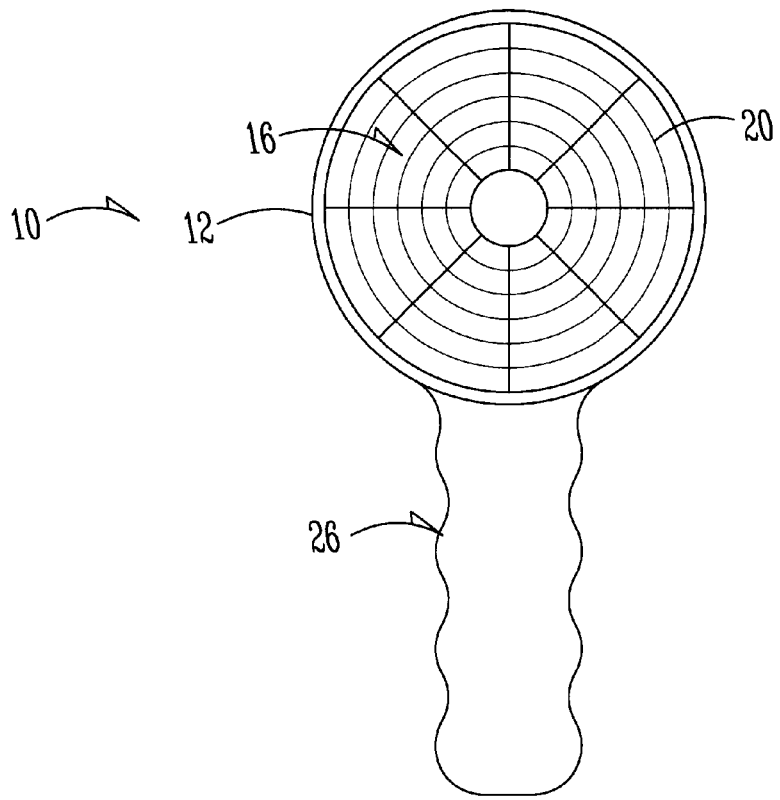
FIG. 2 is a front elevational view of the drying apparatus of FIG. 1.
Figure 3:
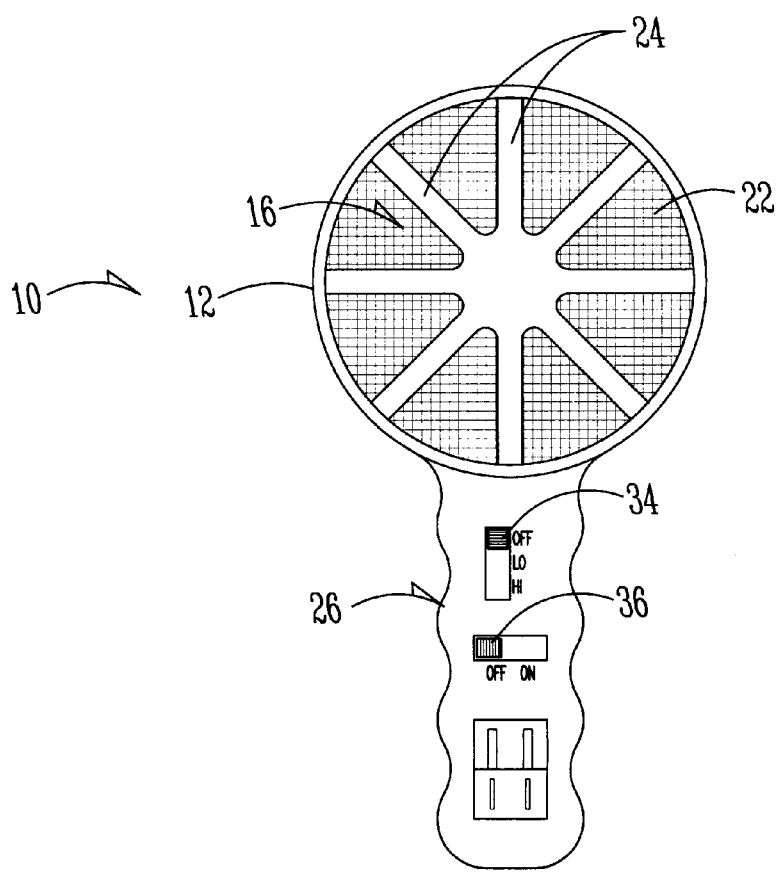
FIG. 3 is a rear elevational view of the drying apparatus.

As shown in FIG. 2, a grid 20 having a plurality of annular walls is positioned to cover the air outlet 16. The grid 20 is preferably a one-piece article which can be made (at least in part) of a suitable lightweight plastic material, the same as the housing 12 of the drying apparatus 10. At the air inlet (see FIG. 3) a caged material 22 encloses the air outlet 14 and is disposed between a plurality of radially extending ribs 24 provided for structural reinforcement of the housing 12. It can be appreciated that both the air inlet 14 and outlet 16 are enclosed to prevent injury to the child during use of the drying apparatus 10.

Figure 4:
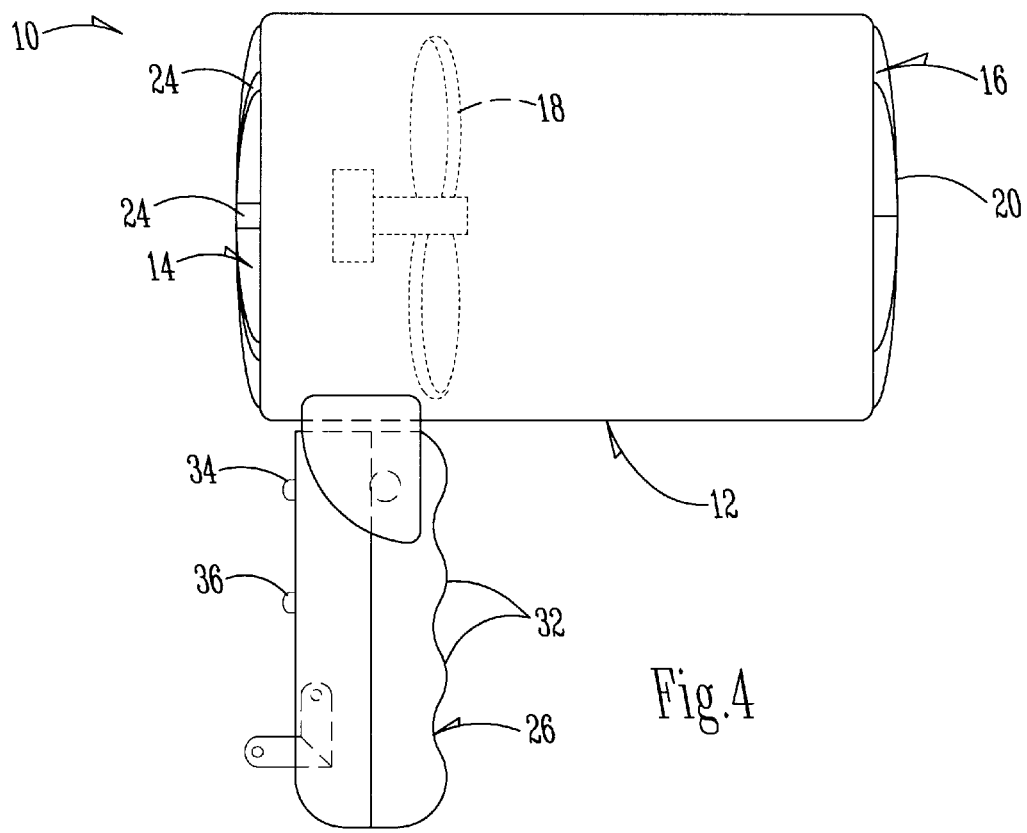
FIG. 4 is a side elevational view of the drying apparatus, showing the handle in a projected position.
Figure 5:
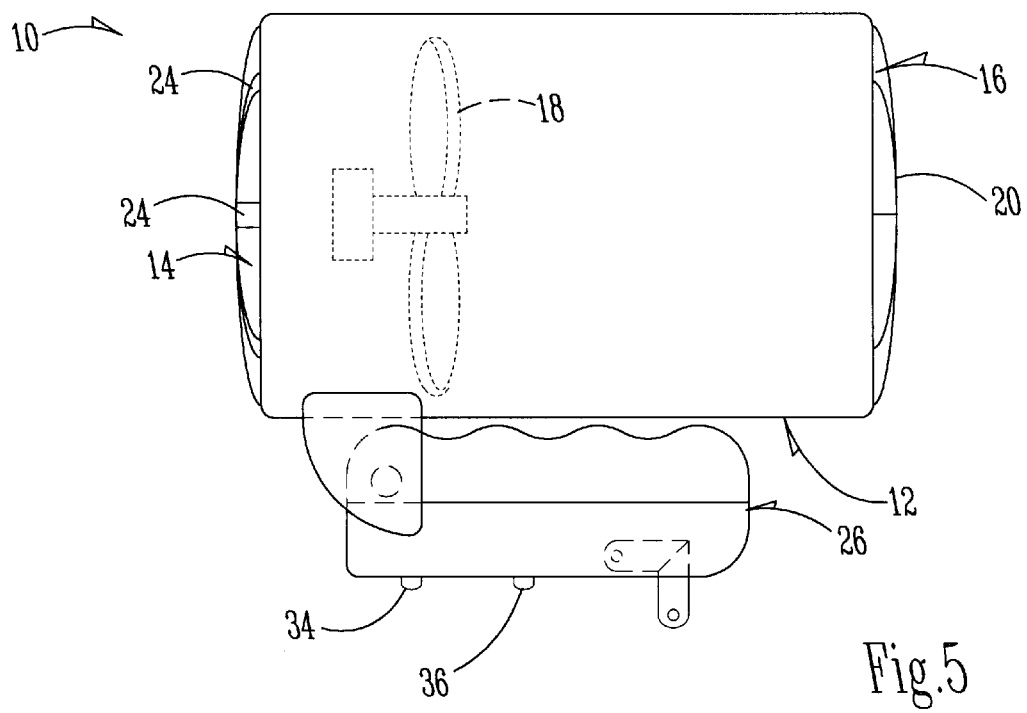
FIG. 5 is a side elevational view of the drying apparatus, showing the handle in a retracted position.

As shown in FIGS. 4 and 5, the drying apparatus 10 includes an elongated handle 26 hinged about a pin 28 extending between two rails 30 attached to the housing 12. The handle 26 rotates between a projected position and a retracted position. In the projected position, as shown in FIG. 4, the handle 26 extends perpendicular to the housing 12. In the retracted position, as shown in FIG. 5, the handle is positioned parallel to the longitudinal axis of the housing 12. Hinging the handle 22 in such a manner allows the drying apparatus 10 to form a compact size that facilitates easy transport and storage in a diaper bag or similar article. In the preferred embodiment, the handle also includes a plurality of ridges 32 that form a finger mold, making the handle 26 easy to grip for the caregiver.

The handle 26 of the drying apparatus 10 includes a conventional slidably mounted switch 34 for controlling the flow or air discharged from the drying apparatus. To control the speed of the impeller 18, the caregiver moves the switch from the OFF position to either the LOW or HIGH speed setting. In accordance with another feature of the invention, the drying apparatus 10 includes a safety lock 36 that the caregiver can move between an OFF and ON position to guard against inadvertent activation of the drying apparatus 10 by the child.

The drying apparatus 10 can be used with AC power by connecting the motor internal to the drying apparatus 10 with a source of AC power by a power cord (not shown). For purposes of convenience, the power cord may be stored internally in the handle and accessed through a removable door (not shown). In its preferred form, however, the drying apparatus 10 includes a rechargeable power source so that the drying apparatus may be operated free of any power cord. As shown in FIG. 1, the drying apparatus 10 may be plugged directly into an AC outlet for charging, with an adapter and charging unit stored internally to the dryer. In an alternative embodiment, the drying apparatus can be placed in a cradle (not shown) or similar device for charging. The drying apparatus 10 can also be charged from a 12 volt power source in an automobile, using a cord and charging unit well known in the art.

The method of the present invention for treating diapered areas on a child's skin to prevent diaper dermatitis makes use of the drying apparatus 10 described above. In the preferred method, the caregiver first removes the soiled diaper worn by the child. Next, the diapered area of the child's skin is washed. Then, the portable drying apparatus 10 described above is used by the caregiver to dry the diapered area of the child's skin by directing the flow of air toward the diapered area. It can be appreciated that this flow of air is at ambient or slightly above ambient air temperatures. Although ambient air temperature is preferred, air at 5° F. above ambient air temperature is acceptable. The method of the present invention expedites the drying process, while eliminating the risk that the child's skin will become irritated or burned from exposure to air at elevated temperatures.

The caregiver can also apply, if desired, a moisturizing lotion or powder to the diapered area after drying is complete. And, of course, a clean diaper can then be put on the child.

A general description of the present invention as well as a preferred embodiment of the present invention has been set forth above. Those skilled in the art to which present invention pertains will recognize and will be able to practice additional variations in the method and apparatus described which fall within the teachings of this invention. Accordingly, all such modifications and additions are deemed to be within the scope of the invention which is to be limited only by the claims appended hereto.

What is claimed is:

1. A method of treating the diapered area of a child's skin to prevent diaper dermatitis, the method comprising:

removing a diaper worn by the child;

washing the diapered area of the child's skin;

providing a portable drying apparatus that includes a housing having an air admitting inlet and an air discharging outlet, a rotary impeller mechanism disposed within the housing for producing and discharging a flow of air at or near ambient air temperature through the air outlet, and a handle mounted to the housing; and drying the diapered area of the child's skin by directing the flow of air at or near ambient air temperature toward the diapered area.

2. The method of claim 1 further comprising the step of applying a moisturizing lotion to the diapered area of the child's skin after drying the diapered area.

3. The method of claim 1 further comprising the step of applying a power to the diapered area of the child's skin after drying the diapered area.

4. The method of claim 1 further comprising the step of putting a clean diaper on the child's diapered area after drying the diapered area.

5. The method of claim 1 wherein the handle being hingeably mounted to the housing and moveable between a projected position and retracted position.

6. The method of claim 1 wherein the drying apparatus not including a heating element for heating the flow of air.

7. The method of claim 1 wherein the handle having a rubberized gripping surface.

8. The method of claim 7 wherein the gripping surface having a plurality of ridges forming a finger mold.

9. The method of claim 1 further comprising a rechargeable power source for providing power to the rotary impeller mechanism.

10. The method of claim 1 further comprising a grid enclosing the air inlet and a caged section of material enclosing the air outlet, wherein the grid and caged section of material being sized to prevent the child's skin from entering the housing.

11. A portable drying apparatus for use in drying a diapered area of a child's skin to prevent diaper dermatitis, the drying apparatus comprising:

a housing having an air admitting inlet and an air discharging outlet;

a rotary impeller mechanism disposed within the housing for producing and discharging a flow of air through the air outlet; and a handle hingeably mounted to the housing and moveable between a projected position and retracted position;

said drying apparatus having the advantage of discharging the flow of air toward the diapered area of the child's skin at or near ambient air temperature.

12. The drying apparatus of claim 11 wherein the drying apparatus not including a heating element for heating the flow of air.

13. The drying apparatus of claim 11 wherein the handle having a rubberized gripping surface.

14. The drying apparatus of claim 13 wherein the gripping surface having a plurality of ridges forming a finger mold.

15. The drying apparatus of claim 11 further comprising a rechargeable power source for providing power to the rotary impeller mechanism.

16. The drying apparatus of claim 11 further comprising a grid enclosing the air inlet and a caged section of material enclosing the air outlet, wherein the grid and caged section of material being sized to prevent the child's skin from entering the housing.

* * * * *